United States Patent [19]
Maki et al.

[11] Patent Number: 5,580,958
[45] Date of Patent: Dec. 3, 1996

[54] POLYPEPTIDES ENCODING TRANSCRIPTIONAL ACTIVATORS AND USES THEREOF

[75] Inventors: Richard A. Maki; Michael J. Klemsz; Scott R. McKercher, all of San Diego; Antonio Celada, Poway, all of Calif.

[73] Assignee: La Jolla Cancer Research Foundation, La Jolla, Calif.

[21] Appl. No.: 267,190

[22] Filed: Jun. 28, 1994

Related U.S. Application Data

[63] Continuation of Ser. No. 470,862, Jan. 26, 1990, abandoned.

[51] Int. Cl.[6] .................. C07K 14/82; C07K 14/435
[52] U.S. Cl. ........................................................ 530/350
[58] Field of Search ................................. 514/19; 530/350

[56] References Cited

FOREIGN PATENT DOCUMENTS

WO88/06601 9/1988 WIPO.
WO89/02472 3/1989 WIPO.

OTHER PUBLICATIONS

Moreau–Gachelin et al. (1990) "The PU.1 Transcription Factor is the product of the putative oncogene Spi–1", Cell 61:1165–1166.

Moreau–Gachelin et al Oncogene 4:1449–1451 (1988).

Pettersson and Schaffner Gene & Dev. 1:962–972 (1987).

Serfling, et al, Embo Journal 8:465–473 (1989).

Boulukos et al Embo Journal, vol. 7 No. 3, 697–705 1988.

Klemsz et al Cell vol. 61, 113–124, 1990.

Shaw et al, Sci. 241:202–205 (1988).

Moreau–Gachelin et al., The putative oncogene Spi–1: murine chromosomal localization and transcriptional activation in murine acute erythroleukemias Nature 331:277–284 (1989).

Guarente, Leonard. Cell. 52:303–305 (1988).

Karim, F. D. et al. Genes & Development. 4(9):1451–1453 (1990).

*Primary Examiner*—George C. Elliott
*Assistant Examiner*—Scott David Priebe
*Attorney, Agent, or Firm*—Campbell & Flores LLP

[57] ABSTRACT

The invention provides a purified polypeptide having substantially the same amino acid sequence and activity as the protein having the amino acid sequence of FIG. 1, or a characteristic fragment thereof. The polypeptide is a transcriptional activator. Nucleic acids encoding the polypeptide and uses are also provided.

5 Claims, 1 Drawing Sheet

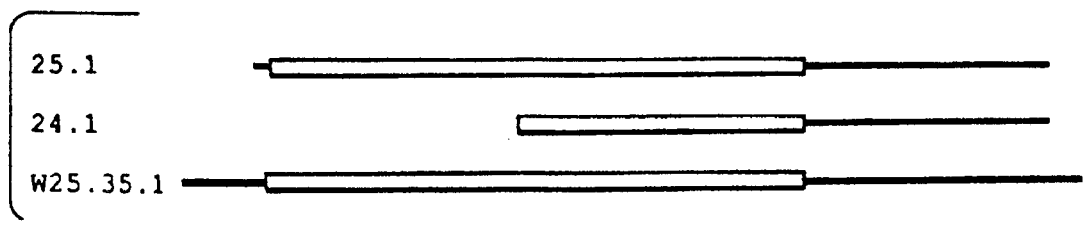

FIG. 1A

```
                                          CTCAGGGGGCAG     12
GCCTGAGCCCTGCGTCTGACCCACGACCGTCCAGTCCCCCGACGGGGCACCTGGTCCTGA     72
GGGGGATCCGCCTTGATCCCCACCGAAGCAGGGGATCTGACCAACCTGGAGCTCAGCTGG    132
      M   L   Q   A   C   K   M   E   G   F   S   L   T   A   P   P   S   D   D   L      20
ATGTTACAGGCGTGCAAAATGGAAGGGTTTTCCCTCACCGCCCCTCCATCGGATGACTTG    192
      V   T   Y   D   S   E   L   Y   Q   R   P   M   H   D   Y   Y   S   F   V   G      40
GTTACTTACGATTCAGAGCTATACCAACGTCCAATGCATGACTACTACTCCTTCGTGGGC    252
      S   D   G   E   S   H   S   D   H   Y   W   D   F   S   A   H   H   V   H   N      60
AGCGATGGAGAAAGCCATAGCGATCACTACTGGGATTTCTCCGCACACCATGTCCACAAC    312
      N   E   F   E   N   F   P   E   N   H   F   T   E   L   Q   S   V   Q   P   P      80
AACGAGTTTGAGAACTTCCCTGAGAACCACTTCACAGAGCTGCAGAGCGTGCAGCCCCCG    372
      Q   L   Q   Q   L   Y   R   H   M   E   L   E   Q   M   H   V   L   D   T   P     100
CAGCTACAGCAGCTCTATCGCCACATGGAGCTGGAACAGATGCACGTCCTCGATACTCCC    432
      M   V   P   P   H   T   G   L   S   H   Q   V   S   Y   M   P   R   M   C   F     120
ATGGTGCCACCCCACACCGGCCTCAGTCACCAGGTTTCCTACATGCCCCGGATGTGCTTC    492
      P   Y   Q   T   L   S   P   A   H   Q   Q   S   S   D   E   E   E   G   E   R     140
CCTTATCAAACCTTGTCCCCAGCCCACCAGCAGAGCTCAGATGAGGAGGAGGGTGAGAGG    552
      Q   S   P   P   L   E   V   S   D   G   E   A   D   G   L   E   P   G   P   G     160
CAGAGCCCTCCCCTGGAGGTGTCTGATGGAGAAGCTGATGGCTTGGAGCCTGGGCCAGGT    612
      L   L   H   G   E   T   G   S   K   K   K   I   R   L   Y   Q   F   L   L   D     180
CTTCTGCACGGGGAGACAGGCAGCAAGAAAAAGATTCGCCTGTACCAGTTCCTGCTGGAC    672
      L   L   R   S   G   D   M   K   D   S   I   W   W   V   D   K   D   K   G   T     200
CTGCTGCGCAGCGGCGACATGAAGGACAGCATCTGGTGGGTGGACAAGGACAAAGGTACC    732
      F   Q   F   S   S   K   H   K   E   A   L   A   H   R   W   G   I   Q   K   G     220
TTCCAGTTCTCGTCCAAGCACAAGGAGGCGCTGGCGCACCGCTGGGGCATCCAGAAGGGC    792
      N   R   K   K   M   T   Y   Q   K   M   A   R   A   L   R   N   Y   G   K   T     240
AACCGCAAGAAGATGACCTACCAGAAGATGGCGCGCGCGCTGCGCAACTACGGCAAGACA    852
      G   E   V   K   K   V   K   K   K   L   T   Y   Q   F   S   G   E   V   L   G     260
GGCGAGGTGAAGAAAGTCAAGAAGAAGCTCACCTACCAGTTCAGCGGCGAGGTGCTGGGC    912
      R   G   G   L   A   E   R   R   L   P   P   H                                     272
CGTGGGGGCCTGGCCGAGCGGCGCCTCCCGCCCCACTGATCGCCCGCAGAGACCGCCAGG    972
CTCCTGGACCCCGCCGGCCATAGCATTAACCCGTCGCCCGGCCCGGACACAGGGAGGACA   1032
TTCCCAGGGCCGAGGCAGGACTGGGGCCCGGCCTCGCCCTCCCATGCCCGGCCTGGCCC    1092
GCCCCACCCGCTTTGCCTCCCACCAGGACTCTAGCCCGCTCCAAGGGCCGCCTGGGCCTC   1152
GGACCTCAACCGAGGGTCAGCCTGGCTTAGTGGCCACGGTGCTTCCTTGGGAGTCTGGCG   1212
CTGGCACCTTTTTGTATATTGAATGCTTTTTAAAAGCTCTTCCTCCCCATCCCCTCATT   1272
AACCACTAAAGACAAGTAAAATTATTGACAGCTATTCTCCC                     1313
```

POLYPEPTIDES ENCODING TRANSCRIPTIONAL ACTIVATORS AND USES THEREOF

GOVERNMENT SUPPORT

This work was supported by U.S. Public Health Service Grant AI20194, the Government may have certain rights in the invention.

This application is a continuation of application Ser. No. 07/470,862, filed Jan. 26, 1990, now abandoned.

FIELD OF THE INVENTION

This invention relates to novel transcriptional activators.

REFERENCES

Throught this application various publications are referenced by author name and date of publication. Full citations for these publications may be found at the end of the specification immediately preceding the claims. The disclosures of these publications in their entireties are hereby incorporated by reference into this application in order to more fully describe the state of the art to which this invention pertains.

BACKGROUND OF THE INVENTION

The transcription of eukaryotic genes is regulated by specific DNA binding proteins that assemble on cis-acting DNA sequences in both promoters and enhancers (reviewed in Maniatis et al., 1987; Jones et al., 1988; Ptashne, 1988; Struhl, 1989). Many of these DNA binding proteins are ubiquitous in their expression and probably serve a general role in gene transcription. Others are restricted in their expression to one or a few cell types. Several examples have been documented in which the expression of this latter type of DNA binding protein correlates with expression of genes to which they bind (Staudt et al., 1988; Müller et al., 1988; Scheidereit et al., 1988; Bodner et al., 19889; Frain et al., 1989). The biochemical characterization of these cell type specific activators of gene expression will provide a critical step in our understanding of gene regulation.

Recently, a novel genetic approach was used to isolate a variant of simian virus 40 (SV40) in which growth was restricted to CV-1 cells and lymphoid cells (Pettersson and Schaffner, 1987). This variant was selected from an SV40 construction that lacked the 72 bp enhancer region. Characterization of this variant revealed that a duplicate region containing a purine rich sequence called the PU box (5'-GAGGAA-3') was able to substitute for the deleted wild type enhancer. A nuclear activity present only in T-cells and B-cells bound to the PU box. However, a specific protein was not shown to be responsible for the activation of transcription through the PU box. A PU box was independently confirmed in both human and mouse T-cells associated with expression of IL-2 (Serfling et al.; Shaw et al.). While it was shown that mutation in the PU box resulted in up to an 85% reduction in transcription and a factor designated NFAT-1 bound the PU box, it was not shown that NFAT-1 was responsible for the activation of transcription through the PU box.

The present invention describes a DNA binding protein, PU.1, that may be related to this lymphoid specific enhancer activity. The PU.1 protein binds to the PU box, is a transcriptional activator and is expressed in macrophages and B cells. Importantly, since PU.1 is not present in T-cells it represents a novel protein and demonstrates, for the first time, a family of transcriptional activators, expressed in different cell types which recognize the PU box. Thus, this invention satisfies a critical need to find cell specific transcription regulators and relationships between these regulators, especially in those cells which mediate the immune response.

SUMMARY OF THE INVENTION

The invention provides a purified polypeptide having substantially the same amino acid sequence and activity as the protein having the amino acid sequence of FIG. 1, or a characteristic fragment thereof. The polypeptide is a transcriptional activator. Nucleic acids encoding the polypeptide and uses are also provided.

BRIEF DESCRIPTION OF THE FIGURE

FIG. 1 shows DNA sequence of PU.1. A) A diagram of the two original phage clones, lambda 25.1 and lambda 24.1, and the full length cDNA clone, W25.35.1, isolated from a WEH1-3 cDNA library. The open box represents the coding sequence while the black line represents the non-coding sequence. B) DNA sequence of the full length PU. 1 gene and the predicted amino acid sequence. Start points for the original two clones are nucleotide 117 for lambda 25.1 and nucleotide 517 for lambda 24.1.

DETAILED DESCRIPTION OF THE INVENTION

The invention provides a purified polypeptide having substantially the same amino acid sequence and activity as the protein having the amino acid sequence of FIG. 1, or a characteristic fragment thereof. The polypeptide can have substantially the sequence shown in FIG. 1 beginning with methionine at position 1 and ending with histidine at position 272 or beginning with methionine at position 7 and ending with histidine at position 272. Alternatively, the first methionine can be cleaved during processing to produce a functional polypeptide.

By "characteristic fragment" is meant any fragment of the polypeptide which is of sufficient length and amino acid diversity to be unique to the polypeptide. The invention provides in FIG. 1 the entire amino acid sequence of PU.1 and a fragment could be made simply by reviewing the sequence and synthesizing the fragment.

By "purified" is meant a polypeptide free of a portion of the contaminants normally associated with the naturally occurring PU.1. The polypeptides which bind the PU box can also be substantially purified of essentially all the contaminants associated with the naturally occurring polypeptides.

The invention also identifies the polypeptide domains which are responsible for DNA binding and transcriptional activation. As stated elsewhere, the amino terminal end of the DNA binding domain is between about amino acid 129 and 200 and the carboxy terminal end is between about amino acid 230 and 267. One skilled in the art could perform further deletions to better define DNA binding and transcriptional activating domain. Since these domains are known, chimeric molecules can be created with one of the domains as is known in the art. For example, the DNA encoding the transcriptional activating domain could be fused with the DNA of a gene encoding a different DNA binding domain. A protein expressed by this hybrid DNA could use non-PU box regions to initiate transcription.

By "PU box" is meant any nucleotide sequence which binds a member of the PU protein family, especially PU.1. The sequence is normally -GAGGAA- but various substitutions which do not effect PU binding are included.

The invention also provides a nucleic acid encoding the polypeptides of the invention. The nucleic acid sequence for native PU.1 is set forth in FIG. 1. Further, host vector systems capable of expressing the polypeptide are provided. The Example teaches methods to express these polypeptides. One skilled in the art could extend these teachings to expression in any suitable host-vector system. Further, these nucleic acids can encode a characteristic portion of the polypeptides of the invention. Thus, the nucleic-acids can be used as probes to the genes encoding the polypeptides, especially PU.1.

It is understood that the PU.1 nucleic acid and encoded polypeptide of FIG. 1 can be modified without significantly affecting the essential activity of the molecules. Therefore, all such modifications are within the scope of the claims.

The invention also provides a polypeptide which activates or enhances transcription and binds to the PU box. Prior to this invention it was not shown that a polypeptide activated transcription after binding to the PU box. It was merely known that factors, i.e. NFAT-1, associated with the PU box but the affect of the factor on transcription was not demonstrated.

The invention provides the first documentation that a family of transcriptional activators bind the PU box. Such a finding could not be demonstrated prior to cloning the gene for PU.1 and the discovery that PU.1 binds the PU box but is not expressed in T-cells. Since other activities which were known to bind the PU box are found in T-cells, the factors are distinct but are members of the same family.

This family discovery allows for a method of detecting polypeptides which activate transcription comprising contacting the polypeptides with a PU box and detecting the presence of the polypeptides which bind to the PU box.

Also provided is a method of activating or enhancing the transcription of DNA containing a PU box in a cell comprising contacting the PU box with an activating polypeptide. The polypeptide can have substantially the same amino acid sequence and activity as the protein having the sequence of FIG. 1, or a characteristic fragment thereof. The DNA can be any gene containing a PU box. The gene can encode a protein selected from the group consisting GM-CSF, G-CSF, IL-1, IL-3, IL-5, TNF-α, TNF-β, and lysozyme. The cell can be a lymphocyte. In the case of PU.1-like polypeptides, B-cells and macrophages are preferred since they contain endogenous PU.1 and PU box.

Finally, a method of preventing or reducing transcription of DNA containing a PU box is provided. The method comprises binding polypeptides which activate transcription by binding the PU box with a ligand which prevents the binding of the polypeptide to the PU box. The ligand can be an antibody.

The results presented here describe the cloning of the gene for a new transcription factor we have named PU.1. Originally, PU was defined as a lymphoid specific transcriptional activity that allowed the growth of an SV40 variant in lymphoid cells (Pettersson and Schaffner, 1987). The activity was shown to bind to a PU box within a duplicated sequence that substitutes for the wild type enhancer in this SV40 variant. However, PU.1 is only expressed in B cells and macrophages but not in T cell lines. This demonstrates that a different PU box binding protein is present in T cells. Preliminary data from our laboratory using the technique of proteolytic clipping (Schreiber et al., 1988) to characterize the PU binding proteins in macrophages, B cells and T cells demonstrates that T cells express a different PU DNA binding protein than is expressed in macrophages and B cells. In this regard, the PU box DNA binding proteins may be somewhat analogous to the Oct binding proteins, which recognize the same DNA core sequence, yet are expressed in a cell type specific manner and are coded for by different genes (Staudt et al., 1986; Sturm et al., 1988; Clerc et al., 1988; Scheidereit et al., 1988; Müller et al., 1988).

Binding of PU.1 to DNA

Experiments conducted to identify the DNA binding domain of PU.1 placed this domain at the carboxy terminal end of the protein. The carboxy terminal 144 amino acids appear to be sufficient for DNA binding. We found no evidence that this amino acid sequence resembled either a zinc finger (Miller et al., 1985), leucine zipper (Landschulz et al., 1988), helix-loop-helix (Murre et al., 1989), antiparallel β sheet (Tanaka et al., 1984), or the SPKK histone motif (Suzuki, 1989). An analysis of the PU.1 protein, however, using either the algorithm of Garnier et al., (1978) or Chou and Fasman (1978) revealed a helix-turn-helix motif in the carboxy terminal half of the protein that resembled the helix-turn-helix motif found in a number of other DNA binding proteins (Pabo and Sauer, 1984). A tri-helical structure, each helix separated by a turn, was identified between the amino acids 207 and 249 of the PU.1 protein. This helix-turn-helix motif did not have significant amino acid sequence homology to homeo-domain containing proteins (Garcia-Blanco et al., 1989; Scott et al., 1989).

The DNA binding domain of PU.1 is related to the ets gene family

A search of known protein sequences with regions of similarity to PU.1 revealed that the carboxy terminal amino acid sequence of the PU.1 protein has significant identity with a region of amino acid sequence in the ets gene family. Within a stretch of 99 amino acids near the carboxy terminus of PU.1 there is 41% sequence identity with 95 amino acids located near the carboxy terminus of mouse-ets-2, human-ets-2 and human-ets-1 proteins. In contrast, there is only a 6% sequence identity between the first 160 amino acids of PU.1 and mouse ets-2. For two other members of the ets gene family, human-erg-1 and human-elk-1, the percent of amino acid identity to PU.1 within the 99 amino acid region is 37% and 38%, respectively.

The v-ets gene was originally identified in the avian leukemia virus E26 which causes erythroblastic and myeloblastic leukemias in chickens (Moscovici et al., 1981; Radke et al., 1982). Although no function for the c-ets protein has been defined, it is found in the nucleus, is phosphorylated, and has affinity for DNA (Boulukos et al., 1988; Fujiwara et al., 1988a; Fujiwara et al., 1988b; Pognonec et al., 1989). Furthermore, it has been shown that mouse ets-1 and ets-2 are expressed in the thymus and may be involved in T cell activation and proliferation (Bhat et al., 1987;Pognonec et al., 1988; Bhat et al., 1989; Seth et al., 1989).

Recently, the region of c-ets-1 with a high degree of amino acid sequence identity with PU.1 was shown to be essential for nuclear localization and DNA binding (Boulukos et al., 1989). Thus, it is likely that common elements within this region are important for DNA binding. When several of the ets proteins were analyzed using the algorithms of Garnier et al. (1978) or Chou and Fasman (1978), however, no helix-turn-helix motif was seen in this region. Thus, despite the sequence similarity, these proteins may employ a different DNA binding motif. Another possibility is that the amino acid identity between PU.1 and ets reflects a novel DNA binding motif. In this regard, there is a conserved repeat (amino acids 214–248) of basic amino acids (lysine or arginine), in a region known to be Important for DNA binding. In the in vitro transcription-translation experiments with PU.1, the Bss H II construction generated a protein that lacked several of these basic amino acids and lost the ability to bind DNA. In the case of c-ets-1, loss of this basic region resulted in loss of DNA binding (Boulukos et al., 1989). Another area in which PU.1 and the members of the ets family exhibit considerable amino acid sequence identity is amino acids 166–182 (PU.1 numbering). A PU.1 mutant protein lacking these amino acids also lacked DNA binding activity.

Transcriptional activation by PU.1

The PU.1 protein is shown to be a transcriptional activator using a series of CAT constructions in which the PU box is inserted upstream of the TK promoter or downstream of the CAT gene. When any of these CAT constructions are co-transfected with the PU pECE expression plasmid an increase in CAT activity is seen. Mutation of the PU box or the substitution of PU.1 protein with the retinoic acid protein, results in no increase in CAT activity. Based on these results, we conclude that PU.1 increases the level of CAT transcription by binding to DNA in a sequence specific manner.

The PU.1 protein has a number of features demonstrating it to be a transcriptional activator. The carboxy terminal 144 amino acids are highly basic and sufficient for DNA binding. The amino terminal 165 amino acids contain a number of elements that have been associated with activation domains of transcription factors. This region of PU.1 is highly acidic with a net negative charge of –23 in the first 165 amino acids. The transcription factors GCN4 (Hope and Struhl, 1986) and GAL4 (Ma and Ptashne, 1987) have also been shown to contain net negative charges that are necessary for transcriptional activation. In addition, within the amino terminal end of PU.1, between amino acids 75 and 93, there is a high concentration of glutamines (31%). Glutamine rich regions have been shown to be important for transcription activation mediated by the transcription factor SP1 (Courey and Tjian, 1988). Whether the glutamine rich region or the net negative charge in the amino terminal half of PU.1 are important for transcriptional activation are currently being assessed.

PU DNA binding proteins are likely involved in the regulation of gene expression. A PU binding activity is known to promote the growth of SV40 in B cells and T cells (Pettersson and Schaffner, 1987), and has been implicated in the expression of the IL-2 gene (Shaw et al., 1988; Serfling et al., 1989). We have determined that putative PU binding sites exist in a number of other genes, which include GM-CSF (Miyatake et al., 1985; Nimer et al., 1988), G-CSF (Nagata et al., 1986), IL-1 (Clark et al., 1986; Furutani, 1986), IL-3 (Cohen et al., 1986), IL-5 (Tanabe et al., 1985; Campbell et al., 1988), TNF-α (Nedwin et al., 1985), TNF-β (Gardner et al., 1987), and lysozyme (Luckow and Schutz, 1989). Results suggest there may be a hierarchy of PU binding sites: PU.1 binds with higher affinity to the TNF-α PU box than the IL-2 PU box.

The following example is intended to illustrate but not limit the invention.

EXAMPLE

Materials and Methods
Isolation of lambda-gt11 Recombinant PU Binding Protein

Recombinant lambda-gt11 clones were isolated from a normal murine macrophage cDNA library (Clontech Laboratories, Inc., Palo Alto, Calif., Catalogue Number ML 1005) using an in situ filter binding technique (Singh et al., 1988). Oligonucleotides were synthesized on a model 380A Applied Biosystems DNA Synthesizer (Foster City, Calif.) and purified using Applied Biosystems oligonucleotide purification cartridges. The probe used to screen the filters was a tetramer of the 33-mer oligonucleotide (5'-GATCCGTC-CCAAGTGAGGAACCAATCAGCATTG-3'), inserted in the Bam HI site of the vector pGEM 1 (Promega Biotec., Inc., Madison, Wis.). The probe was isolated from the plasmid by digesting with Hind III and Ava I, labelled by filling in the ends with $\alpha$-$^{32}$P labelled dNTPs and the Klenow fragment of E. coli DNA polymerase I and separated from the vector on a 8% polyacrylamide gel. Phage were plated at a density of $2 \times 10^4$ plaques per 150 mm plate for the first screening. Four rounds of plaque purification were used to purify the positive clones.

Sequencing of PU.1 Clones

The inserts from the two lambda-gt11 recombinant clones and the clone W25.35.1 were sub-cloned into the Bluescript KS$^+$ vector (Stratagene, Inc., La Jolla, Calif.) and DNA sequencing performed on double-stranded plasmid templates using the dideoxynucleotide method of Sanger (Sanger et al., 1977), according to the Sequenase protocol (U.S. Biochemical, Inc., Cleveland, Ohio). Deletion clones were constructed by the cloning of smaller restriction fragments into the Bluescript KS$^+$ vector. Both strands of DNA were sequenced with G and I reactions to resolve any compression discrepancies. The full length cDNA clone W25.35.1 was isolated from a WEHI-3 cDNA library constructed in ZAP II (Stratagene, catalogue number 936304) by standard methods (Maniatis et al., 1982) using the lambda 25.1 cDNA insert as a hybridization probe. Sequence analysis was performed using the Micogenie computer program (Beckman Instruments, Inc., Palo Alto, Calif.). Protein comparisons were conducted using the homology algorithm of GENEPRO (window=29, matches= 11, Ktup=2, speed=1; score=100) (Riverside Scientifc Enterprises, Seattle, Wash.). The analysis was performed on the sequences in the Protein Identification Resource (National Biomedical Research Foundation) release 22 (September, 1989).

Production of beta-Galactosidase Fusion Protein and Western and Southwestern Analyses Lysogens were prepared from the lambda 25.1 and lambda 24.1 clones as described (Sturm et al., 1988) and the fusion proteins partially purified using anti-beta-galactosidase antibody bound to Sepharose (5 Prime - 3 Prime, Inc., Paoli, Pa.), as described by the manufacturer. Western and Southwestern analyses were carried out as described (Staudt et al., 1988).

Northern Analysis

RNA was isolated from cell lines and mouse tissues as described (Chirgwin et al., 1979). Some samples of RNA were passed over oligo dT. RNA was fractionated on a 1% agarose gel containing formaldehyde (Maniatis et al., 1982) and transferred to nylon membrane as described by the manufacturer (Schleicher & Schnell, Inc., Keene, N.H.). The probes, 25.1 cDNA or L32-4A were labeled by the random oligo method (Pharmacia LKB Biotechnology, Inc., Piscataway, N.J.). Hybridizations were performed at 42° C. for 20 hrs. in buffer containing 50% formamide, 5×SSC, 0.1% SDS, 10 µg/ml salmon sperm DNA and $1 \times 10^6$ cpm/ml of probe. The filters were washed three times with 0.1×SSC, 0.1% SDS for 15 minutes, at 37° C. before exposing to Kodak XAR film. Hybridized probe was removed from the filter by incubating the filter in 10 mM Tris-HCl, pH 8.0, 0.2 mM EDTA for 2 hrs. at 65° C. Bone morrow macrophages were prepared as described (Celada et al., 1989b).

Gel Electrophoresis DNA Binding Assay

For binding reactions, the PU-1 double stranded oligonucleotide was cloned into the Bam HI site of the vector, pGEM 1. This plasmid was digested with Hind III, labelled by filling in the ends with $\alpha$-$^{32}$P labelled dNTPs and Klenow polymerase, digested with Eco RI and a 70 base pair fragment was isolated from a 6% polyacrylamide gel. DNA-binding reactions were carried out for 15 minutes at room temperature in a final volume of 20 µl containing 10,000 cpm of end-labelled PU-1 probe (approximately 200 pg) in a final buffer concentration of 20 mM HEPES, pH 7.9, 75 mM NaCl, 0.5 mM EDTA, 1 mM DTT, 5% glycerol, using 2 µg of poly dI-dC (Pharmacia) and indicated amounts of competitor double-stranded oligonucleotide. Samples were loaded onto 6% polyacrylamide gels (acrylamide: bisacrylamide ratio 30:1) (Mallinckrodt, St. Louis, Mo.) prepared with 0.25×TBE (1×TBE=0.089M TRIS, 0.089M boric acid, 2.5mM EDTA, pH 8.3), 5% glycerol and electrophoresed at 250 volts for 3 hours at 4° C. in 0.25×TBE. Gels were dried onto Whatmann 3MM paper and exposed to Kodak XAR film at room temperature using an intensifying screen.

Methylation Interference Analysis

The methylation interference analysis was performed as described (Celada et al., 1988). The PU-1 oligonucleotide was end-labelled using gamma-$^{32}$P-ATP and T4 polynucleotide kinase and partially methylated with DMS (final concentration 0.05M) for 2.5 minutes at 20° C. Preparative gel-retardation experiments were carried out using the Ly25.1 fusion protein, followed by autoradiography. The bound and free bands were isolated by electroelution using an ISCO concentrator (ISCO, Lincoln, Nebr.), ethanol precipitated, and cleaved with piperidine for 30 minutes at 90° C. The products were analyzed on 20% acrylamide-8M urea sequencing gels and exposed to XAR film at −70° C.

DNase I Protection Analysis

DNase I protection analysis was performed as previously described (Celada et al., 1988). For this analysis we used cloned PU-1 oligonucleotide that had been disolated from the vector pGEM1 (Promega Biotec) and labelled with Klenow polymerase. The purified DNA fragment (20,000 cpm) was incubated for 60 minutes at room temperature in 40 µl of the same buffer as described above for gel retardation analysis and with the indicated amounts of protein. Nuclear extracts from P388 D1 were prepared as described (Celada et al., 1988). DNase I (1 mg/ml-Worthington Grade) was diluted 20-fold in dH$_2$O and incubated at 4° C. for 45 to 60 minutes prior to use in digestion. Diluted DNase I (4 µl) was added to binding reactions for 2.5 minutes, followed by addition of an equal volume of 2×stop buffer (1% SDS, 20 mM EDTA, 40 mM HEPES, 100 mM NaCl, 0.5 mg/ml tRNA). The samples were phenol/CHCl$_3$ extracted, ethanol precipitated and the analysis of the resulting products was carried out on an 8% polyacrylamide-8M urea sequencing gel.

In Vitro Transcription/Translation of PU.1 cDNA

To map the DNA-binding region of the PU.1 protein, in vitro transcribed RNA was made as described by the manufacturer (Promega), from deletion clones created by successive digests of the KS$^+$ plasmid containing the 25.1 insert. RNA was transcribed using T3 RNA polymerase for all constructions except for the Nci construction, which used T7 RNA polymerase. The RNA templates (1–2 µg) were used as mRNA in a rabbit reticulocyte lysate (Promega) to translate in vitro [$^{35}$S] methionine-labelled protein. Protein production was confirmed by SDS-polyacrylamide gel electrophoresis and autoradiography. Gel retardation analysis with the end-labelled PU-1 oligonucleotide was performed directly with 1 µl of the translation mix as described above. The gels were dried and exposed to two sheets of Kodak XAR film in order to distinguish the $^{35}$S label from the $^{32}$P label.

The 3' deletions were generated by the digestion with the indicated restriction enzyme (Xba I, Nar I, Bss H II or Nco I). The 5' deletion was generated by isolating the Nci I fragement, filling in the ends with Klenow polymerase and cloning the fragement into the Eco RV site of the KS$^+$ plasmid. The internal deletion clone Nco I/Kpn I was created by digesting the plasmid p25.1 with Nco I and Kpn I, followed by treating the DNA with mung bean nuclease and religating.

PU.1 Transfection Assays

The PU.1 expression vector, PU pECE, was constructed by ligating the 25.1 cDNA clone into the Eco RI site of the expression vector, pECE (Ellis et al., 1986). The CAT reporter constructions were made as follows: The PU (1×←), PU mut 1 (1×←) and PU mut 1 (1×→) were made by ligating the double stranded oligonucleotides, PU-1 or PU mut 1, into the Bam HI site of the CAT vector, pBLCAT2 (Luckow and Schütz, 1987). The PU (1×→) was made by digesting the PU-1 pGEM clone (see above) with Sma I and Xba I, and directionally ligating this fragment into Sal I digested and Klenow treated, Xba I digested pBLCAT2. The Pu (4×→) and PU (4×←) were made by digesting dimers of the PU-1 oligonucleotide in both orientations in the Bam HI site of the vector pBLCAT3 with Xba I and Xho I, and ligating both dimers into the Xba I site of pBLCAT2. The PU (8×←) was made by ligating Bgl II and Xba I cut monomers in both orientations of PU-1 from pBLCAT3 into the Xba I site of pBLCAT2. The 3' insertions were made by digesting PU (4×→) with Xba I, isolating the tetramer of PU-1, Klenow blunt ending and ligation into the Sma I site of pBLCAT2. Hela cells were transfected by the method of lipofection, according to the recommendations of the manufacturer (Bethesda Research Laboratories, Gaithersburg, Md.) with two modifications; the lipofectin reagent was allowed to equilabrate in DMEM for 10 minutes prior to use, and the cells were incubated for 8–10 hrs. with the lipofectin/DNA complex. These two modifications resulted in a higher level of transfection in Hela cells. Co-transfections contained 1–2 µg reporter vector, 3 µg of PU pECE expression vector, 3 µg of pCH110, a beta-galactosidase expression vector used to measure transfection efficiency (Pharmacia) and KS$^+$Bluescript to a total of 20 µg of DNA. In some experiments the PU pECE construction was replaced by the retinoic acid receptor expression vector RAR pECE (Graupner et al., 1989). CAT assays were performed using a standard protocol (Gorman et al., 1982). Briefly, cells were isolated after 40–48 hours and subjected to three freeze-thaws in dry-ice/ethanol and 37° C. The extract (1–60 µl) was incubated with $^{14}$C-chloramphenical (CAM) and acetyl coenzyme A for 60–120 minutes at 37° C., followed by extraction with ethyl acetate. The ethyl acetate was dried down and the sample resuspended in 20 µl of ethyl acetate for thin layer chromatography.

RESULTS

Isolation of the PU.1 Gene

In our studies on the promoter of the MHC class II I-Aβ gene, we have demonstrated the binding of a nuclear factor to a CCAAT sequence present at −60 to −65 from the transcription start site (Celada et al., 1988). Attempts to isolate the gene for this CCAAT binding factor using an in situ filter binding technique (Singh et al., 1988) have not been successful. This may be due to the finding that this CCAAT binding factor requires two components for efficient binding of the protein to DNA (Celada and Maki, 1989a). While screening a macrophage lambda-gt11 cDNA library with a double stranded multimerized 33-mer oligonucleotide that contained the sequence from −76 to −46 of the MHC class II gene I-Aβ (5'-gatcCGTCCCAAGTGAGGAAC-CAATCAGCATTG-3'), however, we isolated several clones of a DNA binding factor we have named PU.1. An initial screening of 500,000 phage plaques yielded two recombinant clones designated lambda 25.1 and lambda 24.1. As shown below, DNA sequence analysis revealed that both clones code for the same gene. Since the lambda 25.1 insert was larger, it was used in many of the subsequent experiments.

To demonstrate that lambda 25.1 contained a beta-galactosidase fusion protein that had the capacity to bind DNA in a sequence specific manner, a Southwestern blot was performed using a labelled tetramer of the 33-mer as a probe. Bacterial extracts prepared from lambda-gt11 and lambda 25.1 lysogens were fractionated on a 7.5% SDS-polyacrylamide gel, transferred to nitrocellulose and probed with labeled multimerized 33-mer. Only the lane with the lambda 25.1 extract contained a protein able to bind the probe. When a duplicate filter was incubated with a different multimerized oligonucleotide, no signal was seen in either lane indicating that binding to the multimerized 33-mer sequence was specific. The positive filter was subsequently treated with rabbit antiserum to beta-galactosidase and mouse anti-rabbit immunoglobulin horseradish peroxidase conjugate. In the lane containing the lambda 25.1 extract, the slowest migrating species had an apparent molecular size of 150 kDa. The appearance of several bands of lower molecular size are probably the result of degradation of the 150 kDa species. The largest stained band in the lambda-gt11 lane had a molecular size equivalent to beta-galactosidase (M.W.=116, 000). Some breakdown of the beta-galactosidase occurred in this sample resulting in a band at about 69 kDa. These results indicated that the extracts prepared from the lambda 25.1 lysogen contained a beta-galactosidase fusion protein that had a greater molecular size than beta-galactosidase and specifically bound the multimerized 33-mer.

DNA Binding Specificity of the Fusion Protein

A series of methylation interference experiments using the 33-mer and the lambda 25.1 fusion protein revealed that the fusion protein protected the three guanines within the sequence 5'-GAGGAA-3'. A subsequent search of previously described DNA binding activities revealed an activity present in lymphocytes that binds to a purine rich sequence present within the SV40 enhancer (Pettersson and Schaffner, 1987). The binding site for this activity contains the core sequence 5'-GAGGAA-3' and was called the PU box.

In order to determine if the lambda 25.1 fusion protein could bind to the PU box in the SV40 enhancer, a double stranded oligonucleotide (PU-1) was synthesized corresponding to this region of the SV40 enhancer. This oligonucleotide was cloned into the Bam HI site of the plasmid pGEM-1 and subsequently re-isolated as a fragment for the gel electrophoresis DNA binding assay. In addition, for these and subsequent experiments, the lambda 25.1 beta-galactosidase fusion protein was partially purified using anti-beta-galactosidase-Sepharose. This partially purified protein will be referred to as Ly25.1. When the PU-1 fragment was labelled and a gel electrophoresis DNA binding assay performed using Ly25.1, a retarded complex was observed. This complex was effectively competed by a 50 fold molar excess of cold PU-1. Oligonucleotides that contained an altered PU core sequence (PU mut 5) or in which the central two guanines were changed to cytosines within the PU box (PU mut 1) did not effectively compete for binding of Ly25.1 to labelled PU-1. These results suggested that Ly25.1 recognized the PU box in a sequence specific manner. Since Ly25.1 had a higher affinity for the PU box of PU-1 than the PU box in the 33-mer, PU-1 was used in all subsequent experiments.

A search of other nuclear factor binding sites revealed a similarity in the PU box core sequence (5'-GAGGAA-3') with the core sequence of the AP-3 binding site (5'-GTG-GAA-3') (Chiu et al., 1987). When a double stranded oligonucleotide containing the AP-3 binding site was used as a competitor for binding of the Ly25.1 protein to the oligonucleotide PU-1 no competition was observed, even at a 500 fold molar excess. Based on this result we conclude that Ly25.1 is not the transcription factor AP-3.

To delineate the Ly25.1-binding site on PU-1 further, we performed methylation interference experiments using the double stranded PU-1 oligonucleotide. Binding of Ly25.1 to the PU-1 oligonucleotide resulted in the protection of three guanine residues on the coding strand within the core PU sequence. No guanine residues on the noncoding strand were protected. This footprint is identical to a footprint generated by a lymphocyte specific PU box binding protein described earlier (Pettersson and Schaffner, 1987). Thus, the data are consistent with PU.1 being a mouse PU box DNA binding protein.

Comparison of Ly25.1 to a binding activity present in macrophage nuclear extracts In order to determine if the Ly25.1 protein bound to DNA in a manner similar to that of a nuclear factor present in macrophages, the binding pattern of the Ly25.1 protein and the PU binding activity present in macrophages were compared by DNase I footprinting using the cloned double stranded PU-1 oligonucleotide. A DNase I protected region of 16–17 bp centered over the PU box was obtained with both Ly25.1 and a nuclear extract prepared from P388 D1. These data demonstrate that the murine macrophage cell line P388 D1 expresses a nuclear protein that binds to the PU box in a manner similar to that seen for Ly25.1.

DNA Sequence of PU.1

Both the lambda 25.1 and lambda 24.1 cDNA inserts were subcloned into the Bluescript KS$^+$ vector (Stratagene, Inc., La Jolla, Calif.) and sequenced (FIG. 1). In addition, the insert of lambda 25.1 was used to screen a WEHI-3 macrophage cDNA library. The sequence of the longest clone isolated, W25.35.1, was determined and found to be identical to the sequence obtained from clones lambda 25.1 and lambda 24.1 where the sequence overlapped (FIG. 1). Clone lambda 25.1 began with nucleotide 117, while clone lambda 24.1 started at nucleotide 517. Inspection of the PU.1 cDNA sequence, revealed an open reading frame of 816 bases, which codes for a protein of 272 amino acids. This reading frame was also in frame with the fusion protein reading frames of lambda 25.1 and lambda 24.1. Analysis of multiple cDNAs isolated from the WEHI-3 cDNA library were used to characterize the 5' and 3' termini of PU.1. We have assigned the initial methionine residue based on this sequence information. A methionine codon located seven amino acids downstream, however, has a nucleotide sequence flanking the ATG codon that is a better match to the consensus sequence for the initiation of eukaryotic translation (Kozak, 1986). Without additional information defining the sequence of the amino terminal end of the protein, we will call the first methionine codon the start of the protein sequence. A stop codon 63 bases upstream in the same reading frame as the first methionine shows that we have the entire PU.1 coding sequence.

A hydrophilicity plot of the predicted amino acid sequence revealed two major domains. The amino terminal half of PU.1 is slightly hydrophobic, while the carboxy terminal half is hydrophilic. These two domains are separated by a PEST sequence [a region rich in proline (P), glutamic acid (E) serine (S) and threonine (T)] which has been correlated with the increased degradation of intracellular proteins (Rogers et al., 1986). An inspection of the amino acid sequence revealed that the amino terminal 60% of PU.1 is highly acidic (16% aspartic plus glutamic acids, versus 2% lysine plus arginine in the first 165 amino acids), and contains a glutamine-rich region (31%) between amino acids 75 and 93. Both of these components have been linked to the transcriptional activating qualities of several DNA binding proteins (Ptashne, 1988; Kadonaga et al., 1988; Courey and Tjian, 1988). No serine-threonine rich regions were detected, unlike the serine-threonine rich areas found in several other DNA binding proteins (Kadonaga et al., 1987; Sturm et al., 1988;Miyamoto et al., 1988). The carboxy terminal half of the protein is basic. In the 104 carboxy terminal amino acids (aa 169–272), 27 (26%) are either lysine or arginine, whereas 9 (9%) are either aspartic or glutamic acids. Of the 19 lysines that are in PU.1, 18 are located in this carboxy terminal region. As will be shown below, the carboxy half of the protein encodes the DNA binding domain.

Mapping of the DNA Binding Domain

A series of experiments were designed to map the DNA binding domain of the PU.1 protein, using the technique of in vitro transcription and translation of a series of PU.1 constructions. These products were tested in the gel electrophoresis DNA binding assay using the cloned SV40 PU-1 oligonucleotide as a probe (Hope and Struhl, 1985; Sturm et al., 1988). The lambda 25.1 cDNA was inserted into the Blue Script KS$^+$ vector (p25.1) such that sense RNA could be produced in vitro using the T3 promoter and T3 RNA polymerase. RNAs generated from p25.1 and the deletion clones were translated in vitro using a rabbit reticulocyte lysate. The in vitro translated proteins were fractionated by SDS-polyacrylamide gel electrophoresis and proteins of the appropriate size were detected for each deletion.

The results of these experiments demonstrated that the DNA binding activity of the PU.1 protein was localized within the carboxy terminus. When p25.1 was digested with Xba I, which cut in the polylinker just outside of the cDNA insert, a full-length protein (272 aa) was produced in the in vitro transcription-translation system. This protein gave a retarded band in the gel electrophoresis DNA binding assay using the cloned PU-1 double stranded oligonucleotide as a probe. The plasmid, p25.1 was also digested with Nar I, which cut within the coding sequence, such that the in vitro synthesized protein was five amino acids shorter (267 aa) than the full-length protein. The resultant protein bound to the labelled PU-1 fragment as shown by a retarded band in the gel electrophoresis DNA binding assay. Digestion of p25.1 with Bss H II resulted in an in vitro translated protein of 230 aa that no longer bound to the PU-1 fragment. Therefore, we conclude that the 42 carboxy terminal amino acids of the protein are necessary for DNA binding.

The Nci construction, which removed 117 amino terminal amino acids, created a 155 aa in vitro translated product by utilizing an internal methionine (met 115) as a translation start site. The protein generated in this manner bound to the PU-1 probe and gave a retarded band. This result was similar to that achieved with the Ly24.1 fusion protein. Finally, an internal deletion of p25.1 (Nco/Kpn) produced a protein of 172 amino acids that did not bind the cloned PU-1 oligonucleotide.

These results established 5' and 3' boundaries for the DNA binding domain of the PU.1 protein. The 5' deletions and the result from the Ly24.1 clone placed the amino terminal end of the DNA binding domain between amino acid 129 and 200, The 3' deletions placed the carboxy terminal end of the DNA binding domain between amino acid 230 and 267.

Expression of PU.1 mRNA is Tissue-Specific

In order to define the cell type specificity of PU.1 expression, we examined various cell lines and tissues by Northern blot analysis using the PU.1 cDNA as a probe. We found that the PU.1 gene was expressed in the macrophage like cell lines WEHI-3, P388 D1, and WR19 M.1, as well as in bone marrow derived macrophages. The size of this RNA was 1.4 kb, which agrees well with the length of the longest cDNA clone isolated. Since the activation of macrophages is primarily mediated by the lymphokine interferon gamma (IFN gamma), we incubated WR19 M.1 cells and bone marrow derived macrophages in either the presence or absence of IFN gamma (300 IRU/ml) for 24 hours before RNA was isolated. Macrophages treated with IFN gamma under these conditions have been shown to induce I-A antigen expression (Celada and Maki, 1989b). We observed no change in the level of PU.1 expression in these cells after IFN gamma treatment. The PU.1 gene was also expressed in the B cell lymphoma A20-2J, as well as the plasmacytomas 70A and MOPC315 and at a lower level in the plasmacytoma P3. There appeared to be no expression of PU.1 in the mouse fibroblast cell line L929, and interestingly, there was no expression in the T cell line EL4. We extended this analysis to additional T cell lines and found no expression in the T cell lines OH2 and OI6 (Kanagawa, 1988), BW5147 (Ralph, 1973), A32-26 (Kohler et. al., 1977) or in L3 (Glasebrook and Fitch, 1980) (data not shown). When RNA was analyzed from the thymus, however, we observed expression of the PU.1 gene. While not wishing to be bound by the explanation, the PU.1 expression seen in the thymus may be due to a subset of T cells that express PU.1 or by contaminating macrophages or other cells that express PU.1. In other tissues examined, PU.1 was expressed in the spleen as expected, but not in the brain, heart, kidney or lung. Since PU.1 is not expressed in the liver, PU.1 is not the nuclear factor IEFga, which recognizes the sequence 5'-GCGGAA-3' (La Marco and McKnight, 1989). The same blots used for PU-1 hybridization in FIGS. 8A and 8B were subsequently hybridized with a probe for the ribosomal gene L32 (Dudov and Perry, 1984) to ensure that the RNA was not degraded and to control for the amount of RNA added to each lane.

PU.1 is a transcriptional activator

The PU.1 protein was tested for its ability to regulate transcription in Hela cells which were previously shown to lack PU box DNA binding activity (Pettersson and Schaffner, 1987). A series of DNA constructions were made using the vector pBLCAT2 which contains the chloramphenicol acetyltransferase (CAT) gene linked to the thymidine kinase (TK) promoter (Luckow and Schutz, 1987). From one to eight copies of the PU-1 oligonucleotide were inserted both 5' and 3' of the CAT gene, as well as in both orientations. Expression of the PU.1 protein was generated by inserting the lambda 25.1 gene into the vector pECE, which places the expression of a foreign gene under the control of the SV40 early promoter (Ellis et al., 1986). Each CAT construction was co-transfected with the beta-galactosidase expression plasmid pCH110 and with or without the PU pECE expression plasmid. All CAT values were then normalized to the level of beta-galactosidase expression to correct for any differences in transfection efficiency. When the PU pECE plasmid was co-transfected with CAT constructions containing one PU element, CAT activity increased three to four fold (Table I). The orientation of the PU box did not drastically alter the level of CAT activity measured. When four copies of the PU box were inserted upstream of the TK promoter and this construction co-transfected with PU pECE the CAT activity increased four fold. When eight PU boxes were inserted upstream of the TK promoter, CAT activity increased 18 fold in the presence of the PU.1 protein. No increase in CAT activity was seen when the pECE vector or a retinoic acid receptor pECE expression plasmid (Graupner et al., 1989) was co-transfected with the PU box containing CAT vectors, demonstrating that expression of the PU.1 protein was necessary for an increase in CAT activity to be seen. When the vector pBLCAT2 was co-transfected with the PU pECE plasmid, no increase in CAT activity was observed. Thus, only those CAT plasmids containing a PU box could be activated by the PU.1 protein. A consistent increase in CAT activity was observed with plasmids containing the PU-1 or PU mut 1 oligonucleotides as compared to pBLCAT2.

The PU.1 protein was shown not to bind to a PU box in which the two central guanines have been changed to cytosines. This oligonucleotide was inserted into the plasmid pBLCAT2 and CAT activity measured in the co-transfection assay with the PU pECE plasmid. No trans-activation was observed in this experiment, demonstrating that in order for PU.1 protein to increase the level of CAT activity in this assay, it must bind to the DNA.

The effect of placing the PU box downstream of the CAT gene was also determined. In these examples, when four or eight copies of the PU box containing oligonucleotide were placed downstream of the CAT gene and co-transfected with the PU pECE plasmid a modest increase of about three fold in CAT activity was observed. Therefore we conclude, that trans-activation by PU.1 can take place when the PU box is located either upstream or downstream of the CAT gene.

Cloning of Human Gene Encoding PU.1

The PU.1 cDNA insert was used as a probe for a Northern blot of human RNA. An RNA species of 1:4 kb was seen in human RNA from macrophage and B-cell lines. This size RNA corresponds to the same size RNA for PU.1 seen in mouse macrophage cell lines. Therefore, the human PU.1 RNA will crosshybridize with the mouse PU.1 probe. Based on this hybridization result, a human macrophage or B-cell cDNA library can be screened with the mouse PU.1 cDNA as a probe. Positive clones can be characterized and sequenced to determine the level of similarity between mouse PU.1 and human PU.1. This human PU.1 can be used for the same purposes as the mouse PU.1.

Although the invention has been described with reference to the presently-preferred embodiment, it should be understood that various modifications can be made without departing from the spirit of the invention. Accordingly, the invention is limited only by the claims.

TABLE I

Trans-activation by the PU-1 DNA Binding Protein[a]

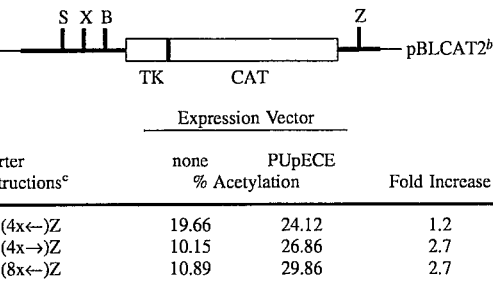

| Reporter Constructions[c] | Expression Vector | | Fold Increase |
|---|---|---|---|
| | none | PUpECE | |
| | % Acetylation | % Acetylation | |
| pBL CAT2 | 2.72 | 2.00 | .7 |
| PU(1x←)B | 5.60 | 19.32 | 3.5 |
| PU(1x→)S/X | 5.54 | 19.97 | 3.6 |
| PU(4x←)X | 9.04 | 34.80 | 3.9 |
| PU(4x→)X | 11.30 | 43.50 | 4.3 |
| PU(8x←)X | 9.14 | 167.54 | 18.3 |
| PU mut 1 (1x←)B | 5.62 | 2.15 | .4 |
| PU mut 1 (1x→)B | 3.36 | 3.97 | 1.2 |
| PU,3'(4x←)Z | 19.66 | 24.12 | 1.2 |
| PU,3'(4x→)Z | 10.15 | 26.86 | 2.7 |
| PU,3'(8x←)Z | 10.89 | 29.86 | 2.7 |

[a]Table I contains the data from a representative experiment. Each reporter construction was tested greater than six times. The level of acetylation was corrected for differences in transfection efficiency using a beta-galactosidase expression plasmid. The PU(8x←)X sample was adjusted for enzyme activity.
[b]Restriction enzyme sites in pBLCAT2 are as follows: B, Bam HI; X, Xba I; S, Sal I; Z, Sma I.
[c]Notation for reporter constructions; oligonucleotide inserted (# of binding sites and orientation of the PU element, arrow to the right indicates 5'-GAG-GAA-3' on coding strand) polylinker insertion point. 3' indicates insertion of oligonucleotides 3' of CAT gene.

REFERENCES

Bhat, N. K., Fisher, R. J., Fujiwara, S., Ascione, R. and Papas, T. S. (1987) Temporal and tissue specific expression of mouse ets genes. Proc. Natl. Acad. Sci. USA 84, 3161–3165.

Bhat, N. K., Komschlies, K. L., Fujiwara, S., Fisher, R. J., Mathieson, B. J., Gregorio, T. K., Young, H. A., Kasik, J. W., Ozato, K. and Papas, T. S. (1989) Expression of ets genes in mouse thymocyte subsets and T cells. J. Immunol. 142, 672–678.

Bodner, M., Castrillo, J. L., Theill, L. E., Deerinck, T., Ellisman, M. and Karin, M. (1988) The pituitary-specific transcriptiion factor GHF-1 is a homeobox- containing protein. Cell 55, 505–518.

Boulukos, K. E., Pognonec, P., Begue, A., Galibert, F., Gesquiere, J. C., Stehelin, D. and Ghysdael, J. (1988) Identification in chickens of an evolutionarily conserved cellular ets-2 gene (c-ets-2) encoding nuclear proteins related to the products of the c-ets proto-oncogene. EMBO J. 7, 697–705.

Boulukos, K. E., Pognonec, P., Rabault, B., Begue, A. and Ghysdael, J. (1989) Definition of an Ets 1 protein domain required for nuclear localization in cells and DNA-binding in vitro. Mol. Cell. Biol. 9, 5718–5721.

Campbell, H. D., Sanderson, S. J., Wang, Y., Hort, Y., Martinson, M. E., Tucker, W. Q. J., Stellwagen, A., Strath, M. and Young, I. G. (1988) Isolation, structure and expression of cDNA and genomic clones for murine eosinophil differentiation factor. Eur. J. Biochem. 174, 345–352.

Celada, A., Shiga, M., Imagawa, M., Kop, J. and Maki, R. A. (1988) Identification of a nuclear factor that binds to a conserved sequence of the I-Aβ gene. J. Immunol. 140, 3995–4002.

Celada, A. and Maki, R. A. (1989a) DNA binding of the mouse class II major histocompatibility CCAAT factor depends on two components. Mol. Cell. Biol. 9, 3097–3100.

Celada, A. and Maki, R. A. (1989b) The expression of I-A correlates with the uptake of interferon- by macrophages. Eur. J. Immunol. 19, 205–208.

Chirgwin, J., Aeyble, A., McDonald, R. and Rutter, W. (1979) Isolation of biologically active ribonucleic acid from sources enriched in ribonuclease. Biochemistry 18, 5294–5298.

Chiu, R., Imagawa, M., Imbra, R. J., Bockoven, J. R. and Karin, M. (1987) Multiple cis-and trans-acting elements mediate the transcriptional response to phorbol esters. Nature 329, 648–651.

Chou, P. Y. and Fasman, G. D. (1978) Empirical predictions of protein conformation. Ann Rev. Biochem. 47, 251–276.

Clark, B. D., Collins, K. L., Gandy, M. S., Webb, A. C. and Auron, P. E. (1986) Genomic sequence for human prointerleukin 1 beta: Possible evolution from a reverse transcribed prointerleukin 1 alpha gene. Nucl. Acids. Res. 14, 7897–7914.

Clerc, R. G., Corcoran, L. M., LeBowitz, J. H., Baltimore, D. and Sharp, P. A. (1988) The B-cell-specific Oct-2 protein contains POU box- and homeo box-type domains. Genes & Dev. 2, 1570–1581.

Cohen, D. R., Hapel, A. J. and Young, I. G. (1986) Cloning and expression of the rat interleukin-3 gene. Nucl. Acids. Res. 14, 3641–3658.

Courey, A. J., and Tjian, R. (1988) Analysis of Sp1 in vivo reveals multiple transcriptional domains including novel glutamine rich activation motif. Cell 55, 887–898. Dudov, K. P. and Perry, R. P. (1984) The gene family encoding the mouse ribosomal protein L32 contains a uniquely expressed intron containing gene and an unmutated processed gene. Cell 37, 457–468.

Ellis, L., Clauser, E., Morgan, D. O., Edery, M., Roth, R. A. and Rutter, W. J. (1986) Replacement of insulin receptor tyrosine residues 1162 and 1163 compromises insulin-stimulated kinase activity and uptake of 2-deoxyglucose. Cell 45, 721–732.

Frain, M., Swart, G., Monaci, P., Nicosia, A., Stampfli, S., Frank, R. and Cortese, R. (1989) The liver-specific transcription factor LF-B1 contains a highly diverged homeobox DNA binding domain. Cell 59, 145–157.

Fujiwara, S., Fisher, R. J., Seth, A., Bhat, N. K., Showalter, S. D., Zweig, M. and Papas, T. S. (1988a) Characterization and localization of the products of the human homologs of the v-ets oncogene. Oncogene 2, 99–103.

Fujiwara, S., Fisher, R. J., Bhat, N. K., Diaz, S. M., Espina, D. L. and Papas, T. S. (1988b) A short-lived nuclear phosphoprotein encoded by the human ets-2 proto-oncogene is stabilized by activation of protein kinase C. Mol. Cell. Bio. 8, 4700–4706.

Furutani, Y., Notake, M., Fukui, T., Ohne, M., Nomura, H., Yamada, M. and Nakamura, S. (1986) Complete nucleotide sequence of the gene for human interleukin 1 alpha. Nucl. Acids. Res. 14, 3167–3179.

Garcia-Blanco, M. A., Clerc, G. C. and Sharp, P. A. (1989) The DNA-binding homeo-domain of the Oct-2 protein. Genes Dev. 3, 739–745.

Gardner, S. M., Mock, B. A., Hilgers, J., Huppi, R. E. and Roeder, W. D. (1987) Mouse lymphotoxin and tumor necrosis factor: Structural analysis of the cloned genes, physical linkage, and chromosomal position. J. Immunol. 139, 476–483.

Garnier, J. (1978) Analysis of the accuracy and implications of simple methods for predicting the secondary structure of globular proteins. J. Mol. Biol. 120, 97–120.

Glasebrook, A. and Fitch, F. W. (1980) Alloreactive cloned T cell lines, I. Interactions between cloned amplifier and cytolytic T cell lines. J. Exp. Med. 151, 876–895.

Gorman, C. M., Moffat, L. F. and Howard, B. H. (1982) Recombinant genomes which express chloramphenicol acetyltransferase in mammalian cells. Mol. Cell. Biol. 2, 1044–1051.

Graupner, G., Wills, K. N., Tzukerman, M., Zhang, X. and Pfahl, M. (1989) Dual regulatory role for thyroid-hormone receptors allows control of retinoic-acid receptor activity. Nature 340, 653–656.

Hope, I. A. and Struhl, K. (1985) GCN4 protein, synthesized in vitro, binds HIS3 regulatory sequences: Implications for general control of amino acid biosynthetic genes in yeast. Cell 43, 177–188.

Hope, I. A. and Struhl, K. (1986) Functional dissection of a eukaryotic transcriptional activator protein, GCN4 of yeast. Cell 46, 885–894.

Hopp, T. P. and Woods, K. R. (1981) Prediction of protein antigenic determinants from amino acid sequences. Pro. Natl. Acad. Sci. 78, 3824–3828.

Jones, N. C., Rigby, P. W. J. and Ziff, E. B. (1988) Transacting protein factors and the regulation of eukaryotic transcription: lessons from studies on DNA tumor viruses. Genes Dev. 2, 267–281.

Kadonaga, J. T., Courey, A. J., Ladika, J. and Tjian, R. (1988) Multiple regions of SP1 modulate DNA binding and transcriptional activation. Science 242, 1566–1570.

Kanagawa, O. (1988) Antibody-mediated activation of T cell clones as a method for screening hybridomas producing antibodies to the T cell receptor. J. Immunol. 110, 169–178.

Kohler, G., Lefkovits, I., Elliott, B. and Coutinho, A. (1977) Derivation of hybrids between a thymoma line and spleen cells activated in a mixed leukocyte reaction. Eur. J. Immunol. 7, 758–761.

Kozak, M. (1986) Point mutations define a sequence flank: the AUG initiator codon that modulates translation by eukaryotic ribosomes. Cell 44, 283–292.

La Marco, K. L., and McKnight, S. L. (1989) Purification of a set of cellular polypeptides that bind to the purine-rich cis-regulatory element of herpes simplex virus immediate early genes. Genes Dev. 3, 1372–1383.

Landschulz, W. H., Johnson, P. F. and McKnight, S. L. (1988) The leucine zipper: A hypothetical structure common to a new class of DNA binding proteins. Science 240, 1759–1764.

Luckow, B. and Schutz, G. (1987) CAT constructions with multiple unique restriction sites for the functional analysis of eukaryotic promoters and regulatory elements. Nucl. Acids. Res. 15, 5490.

Luckow, B. and Schütz, G. (1989) Cell-type specificity of regulatory elements identified by linker scanning mutagenesis in the promoter of the chicken lysozyme gene. Nuc. Acids. Res. 17, 8451–8462.

Ma, J. and Ptashne, M. (1987) Deletion analysis of GAL4 defines two transcriptional activating segments. Cell 48, 847–853.

Maniatis, T., Fritsch, E. and Sambrook, J. (1982) Molecular cloning: A laboratory manual (Cold Spring Harbor, New York: Cold Spring Harbor Laboratory).

Maniatis, T., Goodbourn, S. and Fisher, J. A. (1987) Regulation of inducible and tissue-specific gene expression. Science 236, 1237–1244.

Miller, J., McLachlan, A. D. and Klug, A. (1985) Repetitive zinc-binding domains in the protein transcription factor IIIA from Xenopus oocytes. EMBO J. 4, 1609–1614.

Miyamoto, M., Fujita, T., Kimura, Y., Maruyama, M., Harada, H., Sudo, Y., Miyata, T. and Taniguchi, T. (1988)

Regulated expression of a gene encoding a nuclear factor, IRF-1, that specifically binds to IFN-β gene regulatory elements. Cell 54, 903–913.

Miyatake, S., Otsuka, T., Yokota, T., Lee, F. and Arai, K. (1985) Structure of the chromosomal gene for granulocyte-macrophage colony stimulating factor: comparison of the mouse and human genes. EMBO J. 4, 2561–2568.

Moscovici, C., Samurat, T., Gazzolo, L. and Moscovici, M. G. (1981) Myeloid and erythroid neoplastic responses to avian defective leukemia viruses in chickens and in quail. Virol 113, 765–768.

Müller, M. M., Ruppert, S., Schaffner, W. and Matthias, P. (1988) A cloned octamer transcription factor stimulates transcription from lymphoid-specific promoters in non-B cells. Nature 336, 544–551.

Murre, C., McCaw, P. S. and Baltimore, D. (1989) A new DNA binding and dimerization motif in immunoglobulin enhancer binding, daughterless, MyoD, and myc proteins. Cell 56, 777–783.

Nagata, S., Tsuchiya, M., Asano, S., Yamamoto, O., Hirato, Y., Kubota, N., Oheda, M., Nomura, H. and Yamazaki, T. (1986) The chromosomal gene structure and two mRNAs for human granulocyte colony-stimulating factor. EMBO J. 5, 575–581.

Nedwin, G. E., Naylor, S. L., Sakaguchi, A. Y., Smith, D., Jarrett-Nedwin, J., Pennica, D., Goeddel, D. V. and Gray, P. W. (1985) Human lymphotoxin and tumor necrosis factor genes: Structure, homology and chromosomal localization. Nucl. Acids. Res. 13, 6361–6373.

Nimer, S. D., Morita, E. A., Martis, M. J., Wochsman, W. and Gasson, J. C. (1988) Characterization of the human granulocyte-macrophage colony-stimulating factor promoter region by genetic analysis: Correlation with DNase I footprinting. Mol. Cell. Biol. 8, 1979–1984. Pabo, C. O. and Sauer, R. T. (1984) Protein-DNA recognition. Annu. Rev. Biochem. 53, 293–321.

Pettersson, M. and Schaffner, W. (1987) A purine-rich DNA sequence motif present in SV40 and lymphotropic paporavirus binds a lymphoid-specific factor and contributes to enhancer activity in lymphoid cells. Genes Dev. 1, 962–972.

Pognonec, P., Boulukos, K. E., Gesquiere, J. C., Stehelin, D. and Ghysdael, J. (1988) Mitogenic stimulation of thymocytes results in the calcium-dependent phosphorylation of c-ets-1 proteins. EMBO J. 7, 977–983.

Pognonec, P., Boulukos, K. E. and Ghysdael, J. (1989) The c-ets-1 protein is chromatin associated and binds to DNA in vitro. Oncogene 4, 691–697.

Ptashne, M. (1988) How eucaryotic transcriptional activators work. Nature 363, 683–689.

Radke, K., Beug, H., Kornfeld, S. and Graf, T. (1982) Transformation of both erythroid and myeloid cells by E26, an avian leukemia virus that contains the myb gene. Cell 31, 643–653.

Ralph, P. (1973) Retention of lymphocyte characteristics by myelomas and +—lymphomas: sensitivity to cortisol and phytohemaglutinin. J. Immunol. 110, 1470–1475.

Rodgers, S., Wells, R. and Rechsteiner, M. (1986) Amino acid sequences common to rapidly degraded proteins: The PEST hypothesis. Science 234, 364–368.

Sanger, F., Nicklen, S. and Coulson, A. R. (1977) DNA sequencing with chain-terminating inhibitors. Proc. Natl. Acad. Sci. 74, 5463–5467.

Scheidereit, C., J. A. Cromlish, Gerster, T., Kawakami, K., Balmaceda, C.-G., Currie, R. A. and Roeder, R. G. (1988) A human lymphoid-specific transcription factor that activates immunoglobulin genes is a homeobox protein. Nature 336, 551–557.

Schreiber, E., Matthias, P., Muller, M. M. and Schaffner, W. (1989) Identification of a novel lymphoid specific octomer binging protein (OTF-2B) by proteolytic clipping bandshift assay (PCBA). EMBO J. 7, 4221–4229.

Scott, M. P., Tamkun, J. W. and Hartzell III, G. W. (1989) The structure and function of the homeo-domain. BBA Reviews on Cancer 989, 25–48.

Serfling, E., Barthelmas, R., Pfeuffer, I., Schenk, B., Zarius, S., Swoboda, R., Mercurio, F. and Karin, M. (1989) Ubiquitous and lymphocyte-specific factors are involved in the induction of the mouse interleukin 2 gene in T lymphocytes. EMBO J. 8, 465–473.

Seth, A., Watson, D. K., Blair, D. G. and Papas, T. S. (1989) c-ets-2 proto-oncogene has mitogenic and oncogenic activity. Proc. Natl. Acad. Sci. USA 86, 7833–7837.

Shaw, J-P, Utz, P. J., Durand, D. B., Toole, J. J., Emmel, E. A. and Crabtree, G. R. (1988) Identification of a putative regulator of early T cell activation genes. Science 240, 1759–1764.

Singh, H., LeBowitz, J. H., Baldwin, Jr., A. S. and Sharp, P. A. (1988) Molecular cloning of an enhancer binding protein: Isolation by screening of an expression library with a recognition site DNA. Cell 52, 415–423.

Staudt, L. M., Singh, H., Sen, R., Wirth, T., Sharp, P. A. and Baltimore, D. (1986) A lymphoid-specific protein binding to the octamer motif of immunoglobulin genes. Nature 323, 640–643.

Staudt, L. M., Clerc, R. G., Singh, H., Lebowitz, J. H., Sharp, P. A. and Baltimore, D. (1988) Cloning of a lymphoid-specific cDNA encoding a protein binding the regulatory octamer DNA motif. Science 241, 577–580.

Struhl, K. (1989) Helix-turn-helix, zinc-finger, and leucine zipper motifs for eukaryotic transcriptional regulatory proteins. Trends Biochem. Sci. 14, 137–140.

Sturm, R. A., Das, G., Herr, W. (1988) The ubiquitous octamer-binding protein Oct 1 contains a POU domain with a homeo-box subdomain. Genes Dev. 2, 1582–1599.

Suzuki, M. (1989) SPKK, a new nucleic acid-binding unit of protein found in histone. EMBO J. 8, 797–804.

Tanabe, T., Konishi, M., Mizuta, T., Noma, T. and Honjo, T. (1987) Molecular cloning and structure of the human interleukin-5 gene. J. Biol. Chem. 262, 16580–16584.

Tanaka, I., Appelt, K., Dijk, J., White, S. W. and Wilson, K. S. (1984) 3-A resolution structure of a protein with histone-like properties in prokaryotes. Nature 310, 376–381.

What is claimed is:

1. A polypeptide having the amino acid sequence shown as amino acid residues 129 to 267 in FIG. 1.
2. A polypeptide having the amino acid sequence shown as amino acid residues 1 to 165 in FIG. 1.
3. A polypeptide that is PU.1.
4. The polypeptide of claim 3 having the amino acid sequence shown in FIG. 1 beginning with methionine at position 1 and ending with histidine at position 272.
5. The polypeptide of claim 3 having the amino acid sequence shown in FIG. 1 beginning with methionine at position 7 and ending with histidine at position 272.

* * * * *